United States Patent
Iranitalab et al.

(10) Patent No.: US 9,017,279 B2
(45) Date of Patent: Apr. 28, 2015

(54) METHOD AND APPARATUS FOR PROVIDING HEAT TO INSUFFLATION GASES

(75) Inventors: Pajhand Iranitalab, Pleasanton, CA (US); Xiaodong Xiang, San Jose, CA (US)

(73) Assignee: Stryker Corporation, Kalamazoo, MI (US)

(*) Notice: Subject to any disclaimer, the term of this patent is extended or adjusted under 35 U.S.C. 154(b) by 710 days.

(21) Appl. No.: 12/806,303

(22) Filed: Aug. 10, 2010

(65) Prior Publication Data

US 2011/0082416 A1  Apr. 7, 2011

Related U.S. Application Data

(60) Provisional application No. 61/278,278, filed on Oct. 5, 2009.

(51) Int. Cl.
| | | |
|---|---|---|
| *A61M 13/00* | (2006.01) | |
| *A61M 5/44* | (2006.01) | |
| *A61M 16/10* | (2006.01) | |
| *A61B 17/34* | (2006.01) | |

(52) U.S. Cl.
CPC .............. *A61M 13/003* (2013.01); *A61M 5/44* (2013.01); *A61M 16/1095* (2014.02); *A61B 17/3474* (2013.01); *A61M 2205/364* (2013.01); *A61M 2205/3653* (2013.01); *A61M 2205/8206* (2013.01)

(58) Field of Classification Search
CPC ....... F28F 1/08; A61M 13/00; A61M 13/003; A61M 5/44

USPC .................................................... 604/26, 114
See application file for complete search history.

(56) References Cited

U.S. PATENT DOCUMENTS

| | | | | |
|---|---|---|---|---|
| 5,362,310 | A | * | 11/1994 | Semm ............................. 604/26 |
| 5,385,148 | A | | 1/1995 | Lesh et al. |
| 5,411,474 | A | | 5/1995 | Ott et al. |
| 5,413,092 | A | | 5/1995 | Williams, III et al. |
| 5,605,532 | A | | 2/1997 | Schermerhorn |
| 5,902,251 | A | | 5/1999 | vanHooydonk |
| 6,299,592 | B1 | | 10/2001 | Zander |
| 6,383,177 | B1 | | 5/2002 | Balle-Petersen et al. |

(Continued)

FOREIGN PATENT DOCUMENTS

| | | |
|---|---|---|
| CA | 2 218 108 | 10/1996 |
| DE | 101 52 513 A1 | 5/2003 |
| WO | WO 96/32154 | 10/1996 |

OTHER PUBLICATIONS

Stryker Endoscopy 510(k) Summary of Safety and Effectiveness, Stryker Scope Warmer, dated Jan. 27, 2006 (4 sheets).

(Continued)

*Primary Examiner* — Nicholas Lucchesi
*Assistant Examiner* — Melissa A Snyder
(74) *Attorney, Agent, or Firm* — Flynn, Thiel, Boutell & Tanis, P.C.

(57) ABSTRACT

An insufflator device is provided that connects to a disposable tube set for providing gas to fill an abdominal cavity of a patient to enable surgical procedures. The insufflator tube set includes a warming sheath, a double lumen design, or a heating strip for providing warmth to the insufflation gas being conveyed through the tube set. A method of heating insufflation gases is also provided.

12 Claims, 6 Drawing Sheets

(56) References Cited

U.S. PATENT DOCUMENTS

| | | | |
|---|---|---|---|
| 7,018,331 B2 | 3/2006 | Chang et al. | |
| 2002/0022762 A1* | 2/2002 | Beane et al. | 600/101 |
| 2003/0181857 A1 | 9/2003 | Blake et al. | |
| 2003/0236015 A1* | 12/2003 | Edirisuriya et al. | 439/191 |
| 2004/0102731 A1* | 5/2004 | Blackhurst et al. | 604/26 |
| 2006/0129098 A1* | 6/2006 | Hart et al. | 604/113 |

OTHER PUBLICATIONS

Stryker Endoscopy Summary of Safety and Effectiveness, Laparoscopic CO2 Insufflator, dated Feb. 21, 2001 (3 sheets).

\* cited by examiner

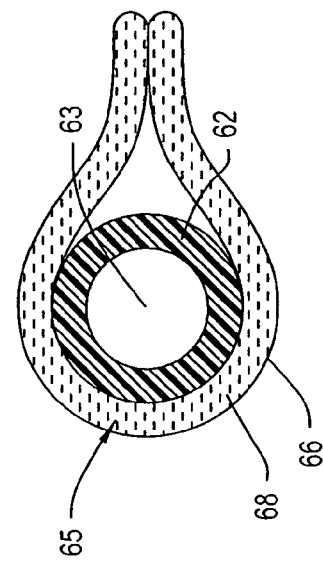
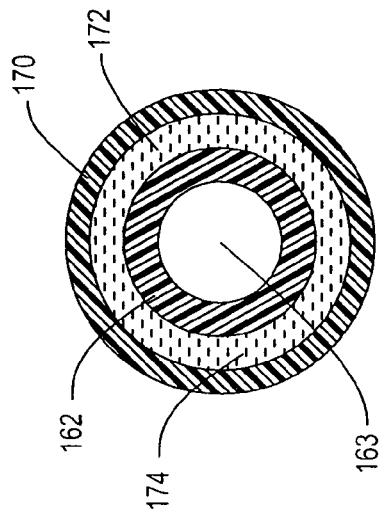
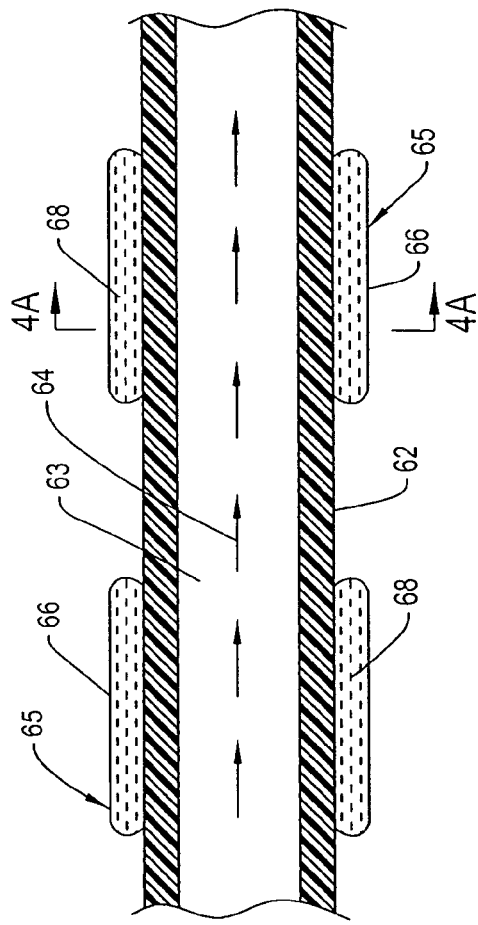
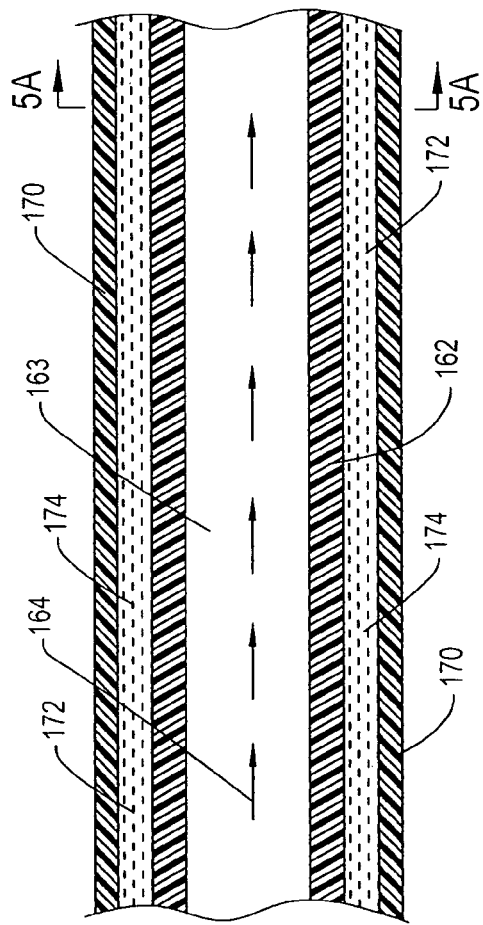

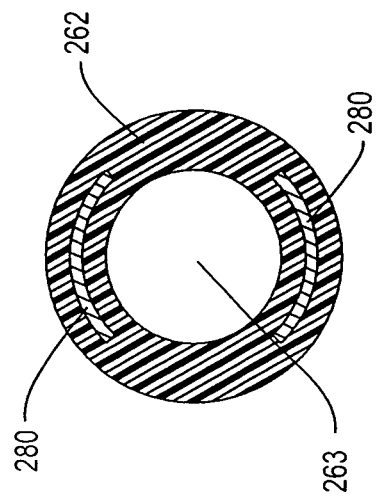
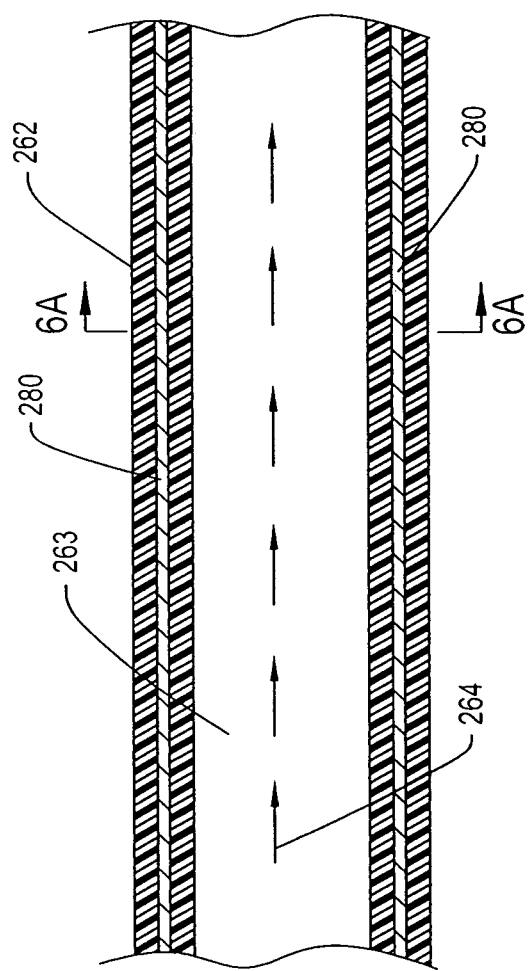

METHOD AND APPARATUS FOR PROVIDING HEAT TO INSUFFLATION GASES

CROSS REFERENCE TO RELATED APPLICATION

This application claims the benefit of U.S. Provisional Application No. 61/278,278, filed Oct. 5, 2009, the disclosure of which is hereby incorporated by reference in its entirety.

FIELD OF THE INVENTION

This invention is generally directed to a method and apparatus for warming gaseous material flowing through an insufflator device.

BACKGROUND OF THE INVENTION

Surgeons have used laparoscopic surgery to perform a variety of procedures. Such surgery, as compared to conventional surgery, reduces patient trauma, decreases patient recovery time, and reduces the amount of post-operative care required.

To perform a laparoscopic operation, a sufficient area for the introduction of a laparoscope and other instruments must be provided by raising the abdominal wall and separating the abdominal wall from the organs enclosed in the peritoneal cavity, commonly referred to as the abdominal cavity. Separation is typically obtained by pressurizing the peritoneal cavity with a suitable gas, typically carbon dioxide. The presence of artificial gas in the peritoneal cavity is referred to as pneumoperitoneum, and is achieved by use of an insufflation device to deliver the gas.

Due to the carbon dioxide or other gas often being depressurized before entry into the peritoneal cavity and the thermal properties of carbon dioxide, the carbon dioxide must be heated and/or the space of the insufflation device within which the carbon dioxide flows must be insulated so that the carbon dioxide gas can retain as much heat as possible during its conveyance to the peritoneal cavity. Heating of the gas in an insufflation device can be quite difficult.

To combat the heat loss of the gas conveyed through an insufflation device, the insufflation tube set presently manufactured and sold by the Assignee includes an electrical coiled wire inside the tube set of the insufflator, often at the distal end of the tube set. The electrical coiled wire is coated with an inert substance and is attached to an electrical lead near the distal end of the tube set. The lead, in turn, has a connector at its proximate end for connection to a temperature port on an insufflation unit. However, the addition of the electrical coiled wire to the tube set raises the cost of the tube set substantially.

In order to obviate, or at least minimize, the disadvantages of known arrangements, including the electrical coiled wire arrangement, the inventors of the present invention have developed unique and less costly heating structures that are effective for heating insufflation gas before it reaches a patient. To achieve such heating, an insufflation tube set is provided which may be connected to an insufflator unit.

One embodiment of the invention includes a warming sheath adjacent, and preferably surrounding, at least a portion of the tube set, preferably near its distal end. Another embodiment includes an electrical heating strip embedded into the wall of the tube set, wherein the heating strip is attached to an electricity source. Yet another embodiment includes an electrical heating strip adjacent the outer surface of the wall of the tube set. Alternatively, the electrical heating strip may be placed inside the tube of the tube set, preferably adjacent its distal end.

A heater in the insufflation unit may also be included to supply heat to the insufflation gas before it enters the tube set. Such a heater is preferably disposed downstream from a valve system which regulates the flow of the insufflation gas to the tube set.

These and other features, advantages, and objects of the present invention will be further understood and appreciated by those skilled in the art by reference to the following specification, claims, and appended drawings.

BRIEF DESCRIPTION OF THE DRAWINGS

FIG. 4 is an enlarged, fragmentary and longitudinal cross-sectional view of a portion of an insufflation tube set.

FIG. 4A is a cross-sectional view of the insufflation tube set taken generally along line 4A-4A in FIG. 4.

FIG. 5 is an enlarged, fragmentary and longitudinal cross-sectional view of a portion of an insufflation tube set.

FIG. 5A is a cross-sectional view of the insufflation tube set taken generally along line 5A-5A in FIG. 5.

FIG. 6 is an enlarged, fragmentary and longitudinal cross-sectional view of a portion of an insufflation tube set.

FIG. 6A is a cross-sectional view of the insufflation tube set taken generally along line 6A-6A in FIG. 6.

Figure 1:
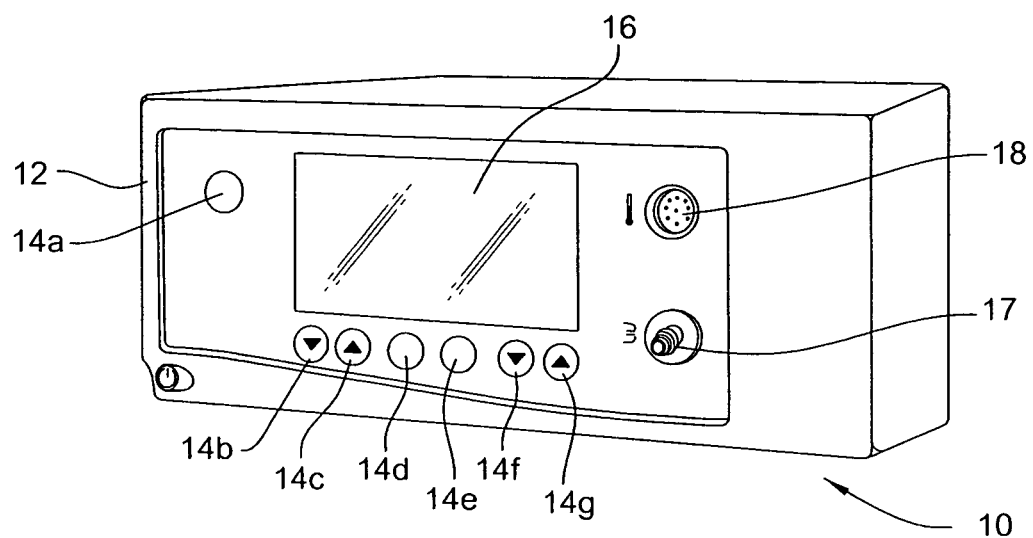
FIG. 1 is a perspective view of an insufflator unit.

Certain terminology will be used in the following description for convenience and reference only, and will not be limiting. For example, the words "upwardly", "downwardly", "rightwardly" and "leftwardly" will refer to directions in the drawings to which reference is made. The words "inwardly" and "outwardly" will refer to directions towards and away from, respectively, the geometric center of the arrangement, and designated parts thereof. Said terminology will include the word specifically mentioned, derivatives thereof, and words of similar import.

DETAILED DESCRIPTION

FIG. 1 shows an insufflator unit 10 including a housing 12 with a plurality of input elements 14a-14g and a display 16. The insufflator unit 10 includes an outwardly projecting flow output port 17 and a temperature connector 18.

Figure 2:
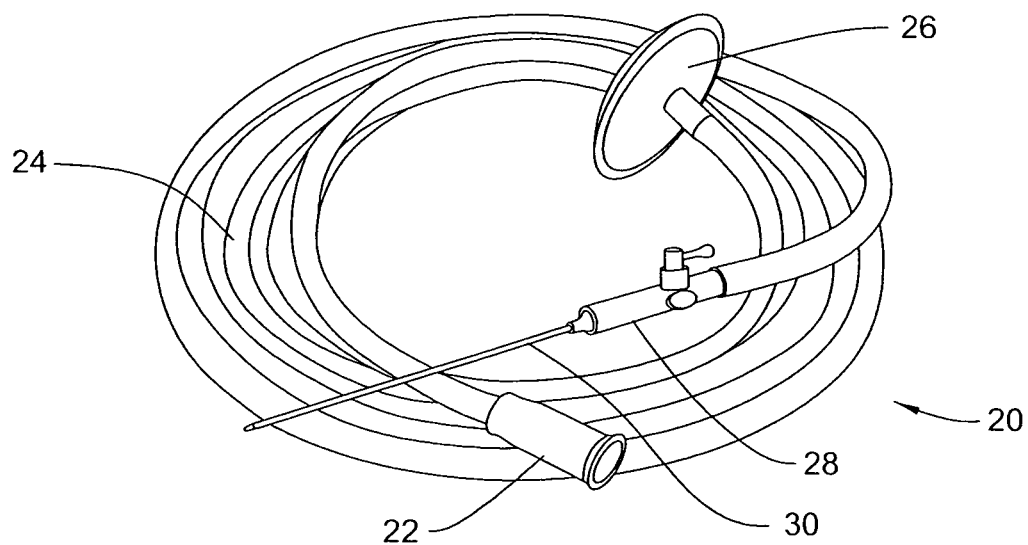
FIG. 2 is a perspective view of an insufflator tube set.

FIG. 2 illustrates an insufflation tube set 20 that includes an input connector 22 at a proximate end for connection of the tube set 20 to the flow output port 17 of the insufflator unit 10. The input connector 22 attaches at its other end to tubing 24. The tubing 24 of the tube set 20 includes a filter 26 provided thereon for filtering any backflow of gas or fluid. The distal end of the tubing 24 has a trocar 28 mounted thereto. The trocar 28 includes a needle-type element 30 for insertion into the abdominal cavity of a patient to perform a surgical procedure. A small incision is made in the body of a patient, and one end of the trocar 28 is inserted into the abdominal cavity.

Figure 3:
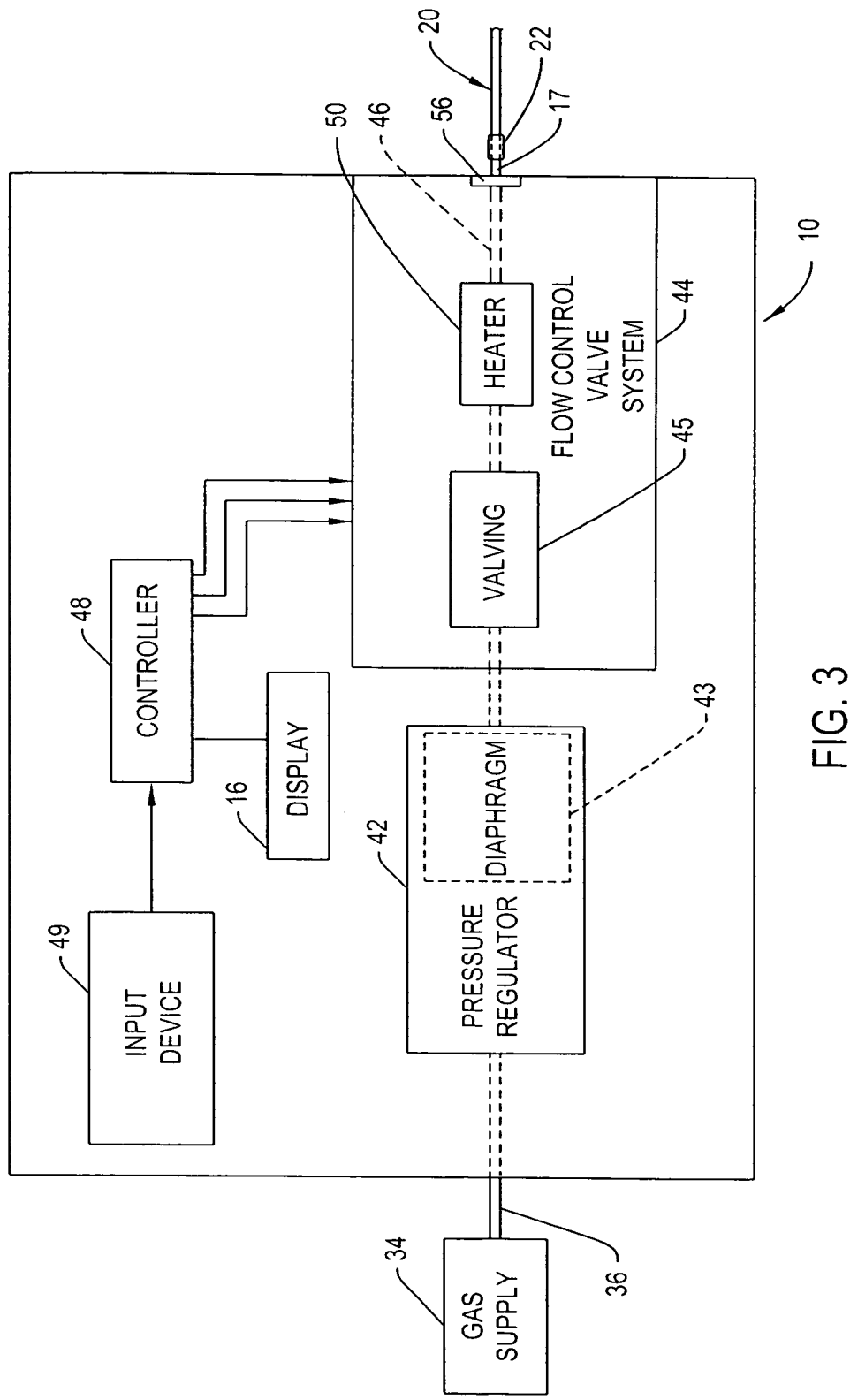
FIG. 3 is a block diagram of an insufflator device connected to a gas supply.

As illustrated in FIG. 3, a gas supply 34 connects to the insufflator unit 10. The insufflator unit 10 controls the passage of gas from the gas supply therethrough and into the tube set 20. The input connector 22 at the proximate end of the tube set 20 connects to the flow output port 17 of the insufflator unit that outputs the flow of gas.

The gas supply 34 shown in the block diagram of FIG. 3 has an output that connects to piping 36 for carrying gas to the insufflator unit 10. The insufflator unit 10 includes a pressure regulator 42 with a diaphragm 43 that connects to a flow control valve system 44. The flow control valve system 44 includes valving 45 and an output pipe 46. The valving 45 includes valve elements that are operated to control the flow of gas or fluid therethrough. The flow control valve system may also include a heater 50 for heating gas from the gas supply 34 before it reaches the tube set 20. Heater 50 may be any type, preferably electrical, that will fit within the housing 12 and is capable of raising the temperature of a gaseous substance such as carbon dioxide flowing through it or by it.

Heater 50 is positioned downstream with respect to the valving 45 within the flow control valve system 44, so that only gas conveyed to the tube set 20 is heated.

The insufflator unit 10 also includes an input device 49. The input device 49 includes input elements 14*a*-14*g*. Input device 49 receives information via input elements 14*a*-14*g* and provides that information to controller 48.

Controller 48 is connected to the flow control valve system 44 and to the display 16. The display 16 displays the condition of the insufflator unit 10. The flow control valve system 44 includes gas outlet port 17 that connects to the output piping 46 of the flow control valve system 44. The insufflator unit 10 may also include a filter 56 disposed inwardly from the gas outlet port 17 and adjacent thereto.

In operation, the gas supply 34 provides a high-pressure fluid, such as $CO_2$, to the pressure regulator 42 of the insufflator unit 10 through piping 36. The pressure regulator 42 outputs gas at a generally constant pressure to the flow control valve system 44.

An operator utilizes the input elements 14*a*-14*g* of the input device 49 to provide various inputs, such as the desired pressure and flow rate for the gas that is to travel through the tube set 20 to a patient. These inputs are communicated from the input device 49 to controller 48. In response to the inputs, the controller 48 provides one or more signals to the valving 45 and heater 50, if included, of the flow control valve system 44 to control various valve elements or the like to adjust the output flow therefrom, and to adjust the temperature of the gas prior to it entering the tube set 20. The output gas travels through piping 46, then through the filter 56, and then through gas outlet port 17 to tube set 20. The gas is conveyed through tube set 20, where it is preferably heated, before exiting the trocar 28 and entering the peritoneal cavity of a patient.

In addition to, or in lieu of, the heater 50 being used to raise the temperature of the insufflation gas, various means may be used in, on, or with the tube set 20 to provide heat to the gas downstream of the insufflation unit 10. These various means of providing heat are preferably used at or near the distal end of the tube set, that is, the end closest to the patient, to ensure that gas at a proper temperature enters the patient.

Figure 4B:
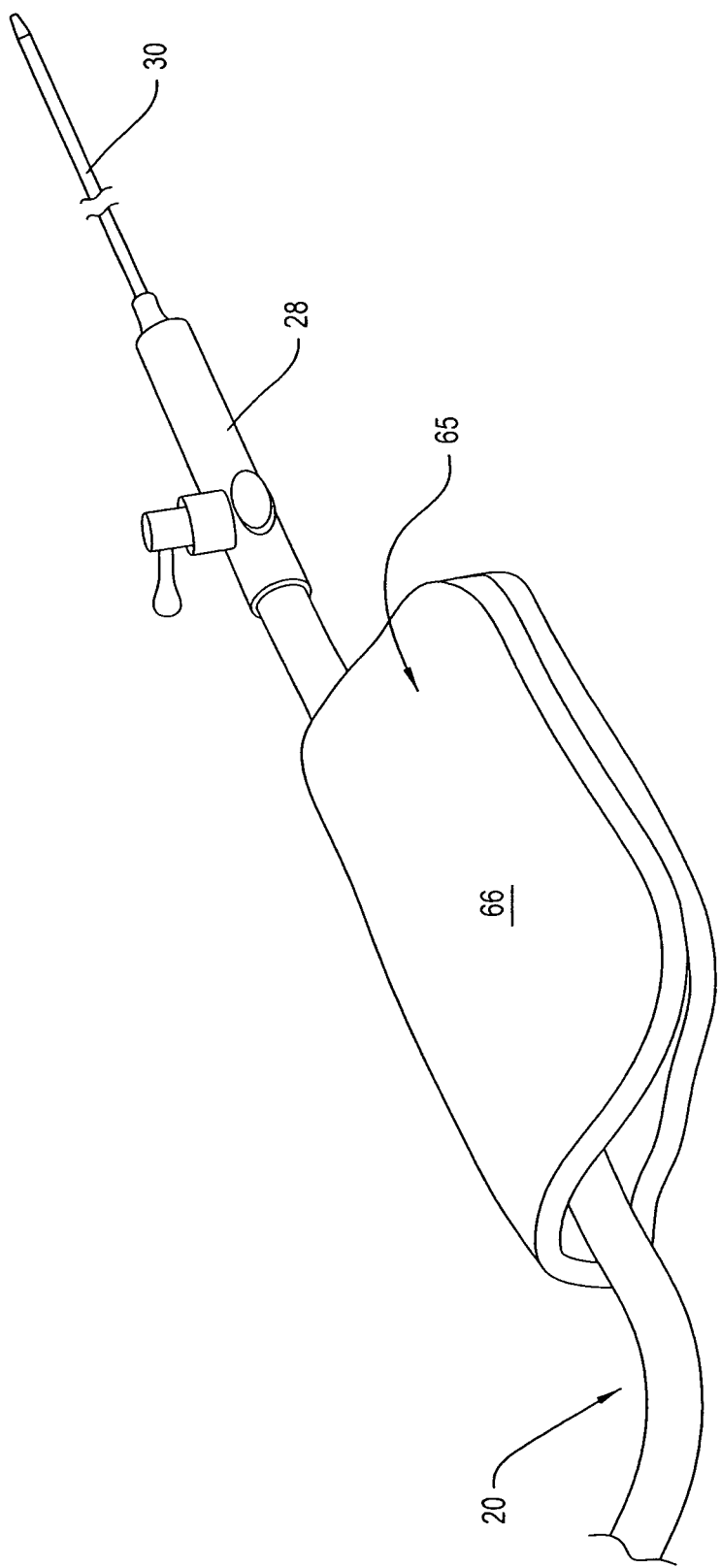
FIG. 4B is a perspective view of the tube set depicted in FIG. 4.

FIGS. 4, 4A, and 4B show one embodiment of a heating device for the tube set 20. The tube set 20, in this embodiment, includes a tube 62 defining a radially centrally located lumen 63 therein. The tube 62 may be of any suitable substance, but is preferably of a flexible substance and more preferably polyethylene terephthalate (PET). The direction arrow 64 shows the direction of flow of gas through the lumen 63. Of course, it is not essential that the gas flow rightwardly, but is depicted as such in the figures for purposes of illustration only. Wrapped about tube 62 on its outer surface are a plurality of, and here two, warming sheaths 65. Warming sheaths 65 may be permanently affixed to the tube 62 or may be provided separately and temporarily affixed to the tube 62. Also, it is not necessary that two sheaths be used for this purpose, as the number of sheaths to be used will depend on the amount of heating desired, the size of the tube set, and the size of the warming sheaths 65. Warming sheaths 65 each include an outer housing layer 66 which is sealed to create a sealed enclosure therein. Enclosed within the housing layer 66 are the contents 68 of the warming sheath 65. The contents 68 of the sheath are two or more reactants that, when combined, react exothermically to release a desired amount of heat. Such reactants are preferably sodium acetate and water, but may be any reactants that react exothermically. The user of the tube set of the embodiment of FIGS. 4, 4A, and 4B may squeeze or bend the sheath to break a fragile barrier between the reactants, causing the reactants to contact one another, resulting in an exothermic reaction. The exothermic reaction provides enough heat to radiate through the warming sheath housing layer 66, through the tube 62, and to warm the gas inside the lumen 63 to the desired temperature before entering the abdominal cavity of the patient. The warming sheaths 65 are preferably disposable, and thus can be thrown away after one use. A preferred warming sheath provides heat to an insufflation gas for 60 to 90 minutes.

The embodiment depicted in FIGS. 5 and 5A includes a double-tube design. In this embodiment, the tube set has an inner tube 162 which defines a radially centrally located first lumen 163. The first lumen 163 is for conveyance of the insufflation gas, the direction of which is shown by direction arrows 164. The tube set of this embodiment also includes an outer tube 170 which is concentric in nature to the inner tube 162, creating a concentric or annular space 172 between the inner tube 162 and the outer tube 170. The double-tube arrangement may extend the entire length of the tube set, but preferably extends only a portion of the entire length. The double tube portion is preferably located near the distal end of the tube set 20. Reactants 174 that react exothermically with each other when combined are disposed in the concentric space 172. The reactants are preferably those described above, which could be sodium acetate and water. When heating of the insufflation gas is desired, the user simply bends a portion of the tube set that includes the double-tube arrangement. Bending of the tube set where the double-tube portion is located breaks a fragile barrier between the reactants, causing the reactants to contact one another, resulting in an exothermic reaction. The heat from the exothermic reaction radiates through the wall of the inner tube 162 and into the first lumen 163, and raises the temperature of the gas flowing through the lumen 163 to a desired temperature before reaching the patient.

FIGS. 6 and 6A show yet another embodiment of a heated tube set. The tube set of this embodiment includes a tube 262, preferably of a flexible material, defining an inwardly disposed lumen 263, which is preferably radially centrally located within the tube 262. Direction arrows 264 show the direction of gas flow through the lumen 263. Embedded within the tube 262 are a plurality of, and here two, electrical heating strips 280. The heating strips 280 provide resistive heating and can be powered by any conventional means. The embodiment of FIGS. 6 and 6A could use, but would not necessarily require use of, the temperature connector 18 of the insufflator unit 10, as the heating strips 280 could be independently powered. Heating strips 280 are preferably co-extruded with the tube 262, thereby creating a permanent construction of the heating strips with respect to the tube 262. It will be appreciated that any number of heating strips may be employed to radiate the desired amount of heat to raise the temperature of the gas conveyed through the tube set.

Figure 7A:
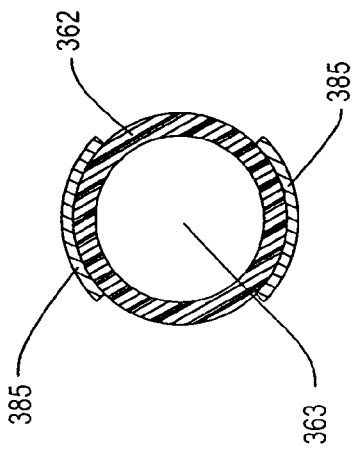
FIG. 7A is a cross-sectional view of the insufflation tube set taken generally along line 7A-7A in FIG. 7.
Figure 7:
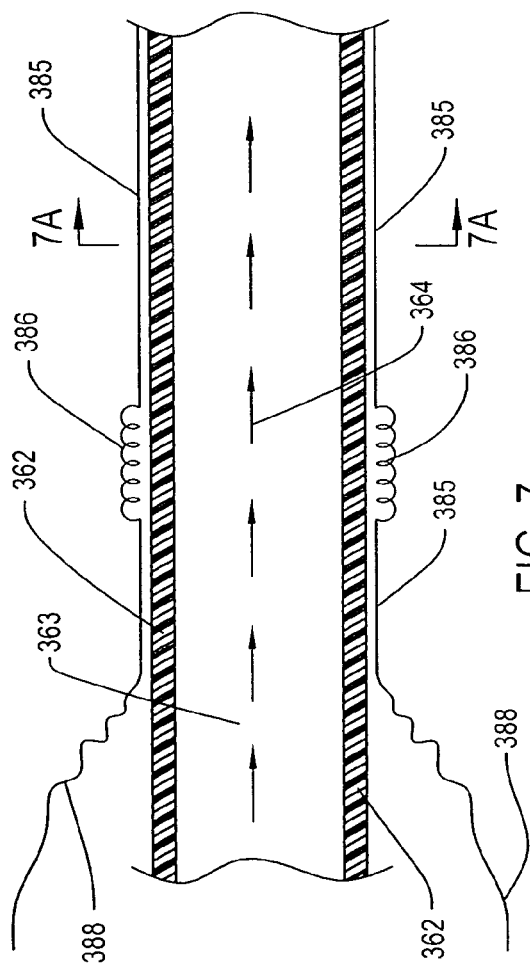
FIG. 7 is an enlarged, fragmentary and longitudinal cross-sectional view of a portion of an insufflation tube set.

Alternatively, the heating strip or strips may be positioned on the outer circumference of the tube or on the inner circumference of the tube. FIGS. 7 and 7A show an embodiment where heating strips 385 are disposed on the outer circumference of the tube 362 of the tube set. Tube 362 defines a lumen 363 which is preferably radially centrally located therein. Direction arrows 364 show the direction of gas flow within the lumen 363. Heating strips 385 are permanently or temporarily attached to the outer surface of the tube 362. Multiple heating strips 385 can be used serially and attached to one another such as by a wire 386, if desired. Lead wires 388 are attached to the heating strips 385, and are also attached to an electricity source such as a battery or electrical controller device.

Figure 8A:
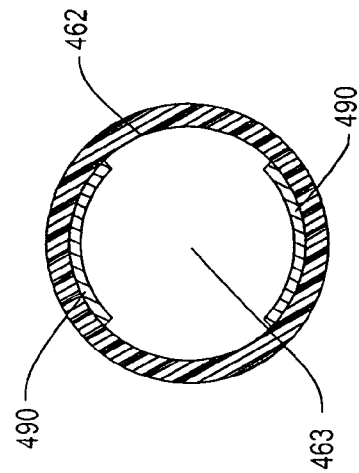
FIG. 8A is a cross-sectional view of an insufflation tube set taken generally along line 8A-8A in FIG. 8.
Figure 8:
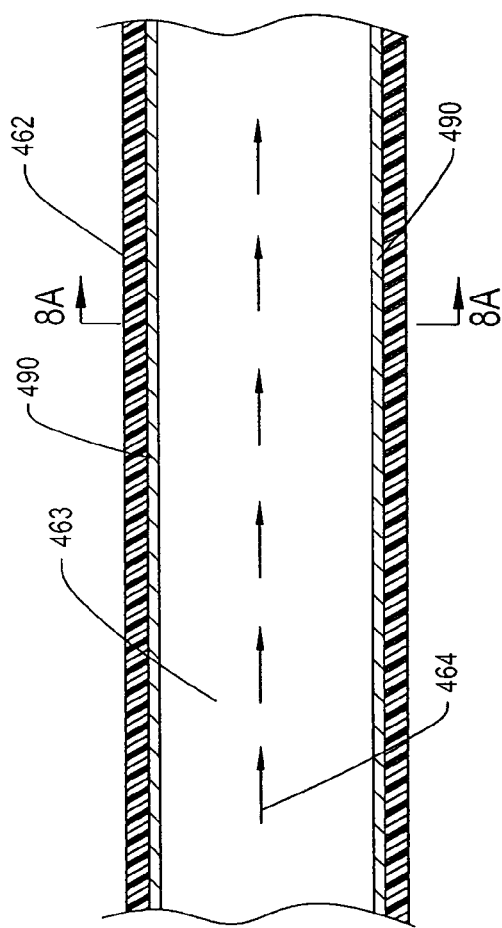
FIG. 8 is an enlarged, fragmentary and longitudinal cross-sectional view of a portion of an insufflation tube set.

FIGS. 8 and 8A show yet another embodiment. The embodiment of FIGS. 8 and 8A includes heating elements located within the lumen of the tube. The tube set of this embodiment includes a tube 462 defining a radially centrally located lumen 463, and heating strips 490. Direction arrows 464 show the direction of gas flow through the lumen 463. Heating elements 490 are similar to those discussed above with regard to the embodiment of FIGS. 7 and 7A, and may be temporarily or permanently affixed to the tube 462 on its inner surface. If temporarily affixed, the heating elements 490 could be separately provided and inserted into the tube 462 at the time of use, in which case heating elements 490 may be sized to be easily inserted by a user but also to abut the inner surface of the tube to stay within the tube during preparation and use of the tube set. Such an arrangement would allow the user to use a single tube set for either heated and non-heated insufflation procedures.

The above embodiments provide a cost-effective and easy-to-use insufflation device with an effective heating source for raising the temperature of the insufflation gas being conveyed through the insufflation device. The costs of the embodiments described above are significantly lower than inclusion of a coiled electrical heating wire inside the insufflation tube set.

Although particular preferred embodiments of the invention are disclosed in detail for illustrative purposes, it will be recognized that variations or modifications of the disclosed apparatus, including re-arrangement of parts, lie within the scope of the present invention.

What is claimed is:

1. An insufflation tube set comprising:
   an input connector for connection to an insufflator output port;
   a tube of a flexible, heat-conductive material configured to extend substantially between an insufflator and a surgery port location in a patient, the tube having a proximal end and a distal end, the distal end being part of a distal portion of the tube, the proximal end connected to the input connector, the tube having a wall with an inner surface and an outer surface, the inner surface of the tube defining a lumen disposed in the tube for transport of a gas from the proximal end to the distal end; and
   a warming element in contact with at least part of the outer surface of the distal portion of the tube for heating a gas as the gas is transported through the lumen, the warming element having a plurality of reactants therein which exothermically react with one another when combined.

2. The insufflation tube set of claim 1, wherein the warming element further comprises a barrier located between and separating the reactants, the barrier being disposed and configured to be broken to allow the reactants to contact each other when heating of an insufflation gas is desired.

3. The insufflation tube set of claim 1, wherein the reactants comprise sodium acetate.

4. The insufflation tube set of claim 1, wherein the warming element comprises a housing in which the reactants reside, the housing being made of polyvinyl chloride.

5. An insufflation device, comprising:
   an input connector for connection to an insufflator;
   a first tube configured to extend substantially between an insufflator and a surgery port location of a patient and having a proximal end connected to the input connector, a distal end spaced from the proximal end, an outer surface, and a passage therein for transport of gas from the input connector to the distal end; and
   a heating element disposed adjacent at least a lengthwise portion of the outer surface of the first tube, the heating element comprising a second tube in which the first tube is disposed, an inner surface of the second tube being spaced from the outer surface of the first tube to define a reactant space in which reactants reside, the reactants reacting exothermically when combined with one another.

6. The insufflation device of claim 5, wherein the second tube is concentric to the first tube so as to define a concentric reactant space therebetween.

7. An insufflation tube set comprising;
   a unitary monolithic flexible insufflation gas transport tube configured to transport gas from an insufflation unit and having a proximal end and a distal end, the flexible tube comprising a wall with an inner surface and an outer surface, the inner surface of the wall defining a gas-conveyance lumen located radially inwardly of the inner surface of the wall;
   an input connector connected to the proximal end of the tube for connection to an insufflation unit; and
   at least one non-wire electrical heating element in contact with at least a portion of the tube wall, the heating element being disposed to be attached to an electricity source and arranged to heat gas flowing through the gas-conveyance lumen when the heating element is activated.

8. The insufflation tube set of claim 7, wherein the at least one non-wire heating element is disposed between the outer surface of the tube wall and the inner surface of the tube wall.

9. The insufflation tube set of claim 7, wherein the at least one non-wire heating element is disposed radially outward of at least a portion of the outer surface of the tube wall.

10. The insufflation tube set of claim 7, wherein the at least one non-wire heating element is disposed radially inward of at least a portion of the inner surface of the tube wall.

11. The insufflation tube set of claim 7, wherein the at least one non-wire electrical heating element is an arcuate strip.

12. The insufflation tube set of claim 8, wherein the at least one non-wire electrical heating element is embedded within the tube wall.

* * * * *